US00PP19690P2

(12) United States Plant Patent
Hambali

(10) Patent No.: US PP19,690 P2
(45) Date of Patent: Feb. 10, 2009

(54) ***AGLAONEMA* PLANT NAMED 'TWYAG0018'**

(50) Latin Name: *Aglaonema hybrida*
Varietal Denomination: TWYAG0018

(75) Inventor: Gregori Garnadi Hambali, Bogor (ID)

(73) Assignee: Kerry's Bromeliad Nursery, Inc., Apopka, FL (US)

( * ) Notice: Subject to any disclaimer, the term of this patent is extended or adjusted under 35 U.S.C. 154(b) by 0 days.

(21) Appl. No.: 11/906,562

(22) Filed: Oct. 3, 2007

(51) Int. Cl.
*A01H 5/00* (2006.01)

(52) U.S. Cl. ..... Plt./376
(58) Field of Classification Search ..... Plt./376
See application file for complete search history.

*Primary Examiner*—Annette H Para
*Assistant Examiner*—S. B McCormick Ewoldt
(74) *Attorney, Agent, or Firm*—Jondle & Associates, P.C.

(57) ABSTRACT

A new *Aglaonema* plant particularly distinguished by having foliage that is dark green and suffused with small coalescing yellow-green spots and blotches, areas adjacent to the midrib often marked with yellow-green, primary veins that are variably tinged with pink, a midrib that is pink throughout, a very dense, leafy, compact plant habit, intermediate in stature and having greyed-orange and orange-white spathes tinged with yellow-green and with light pink apices, is disclosed.

1 Drawing Sheet

Genus and species: *Aglaonema hybrida.*
Variety denomination: 'TWYAG0018'.

BACKGROUND OF THE NEW PLANT

The present invention comprises a new and distinct cultivar of *Aglaonema,* botanically known as *Aglaonema hybrida* and hereinafter referred to by the variety name as 'TWYAG0018'. The new variety originated from an open pollination made in Bogor, West Java, Indonesia between unknown individual plants of *Aglaonema* (species unknown). The new variety was discovered as a single plant within the progeny of the stated open pollination in a controlled environment in Bogor, West Java, Indonesia.

The new variety was created in Bogor, West Java, Indonesia and has been repeatedly asexually reproduced by vegetative cuttings in Apopka, Fla. for two or more generations. The present invention has been found to retain its distinctive characteristics through successive asexual propagations.

SUMMARY OF THE INVENTION

The following are the most outstanding and distinguishing characteristics of the new variety when grown under normal horticultural practices in Apopka, Fla.

1. Foliage is dark green and suffused with small coalescing yellow-green spots and blotches;
2. Areas adjacent to the midrib are often marked with yellow-green;
3. Primary veins are variably tinged with pink and the midrib is pink througout;
4. Very dense, leafy, compact plant habit and intermediate in stature; and
5. Greyed-orange and orange-white spathes tinged with yellow-green and with light pink apices.

DESCRIPTION OF THE PHOTOGRAPH

This new *Aglaonema* plant is illustrated by the accompanying photograph which shows the overall plant habit. The colors shown are as true as can be reasonably obtained by conventional photographic procedures. The photograph is of an 18-month old plant.

DESCRIPTION OF THE NEW VARIETY

The following detailed description sets forth the distinctive characteristics of 'TWYAG0018'. The data which define these characteristics were collected from asexual reproductions carried out in Apopka, Fla. The plant history was taken in January 2007 on 18 month-old plants started from a single four-leaf rooted cutting, still in a vegetative state and grown in Apopka, Fla. Rooted cuttings were planted in 20 cm pots and grown in a greenhouse. The plants were pinched twice. Color readings were taken under natural light. Color references are primarily to the R.H.S. Colour Chart of the Royal Horticultural Society of London (R.H.S.) (2001).

DETAILED BOTANICAL DESCRIPTION

Classification:

*Family.*—Araceae.

*Botanical.*—*Aglaonema hybrida.*

*Common.*—Chinese Evergreen.

Growth:

*Form.*—Symmetrical; wider than tall; new leaves are held upright and mature leaves are held outward.

*Growth and branching habit.*—Very dense, leafy and compact; upright and branched growth habit and intermediate in stature.

*Height* (*from soil to top of leaf plane*).—30 cm to 34 cm.

*Diameter* (*area of spread, as measured from leaf tip to leaf tip across the canopy*).—58 cm to 64 cm.

*Growth rate.*—Typical of commercial *Aglaonema* varieties.

*Vigor.*—Vigorous; plants produce axillary branches and numerous leaves.

*Time to produce a finished flowering plant.*—About 18 months starting from a single 4-leaf rooted cutting with the plants pinched twice in 20 cm pots.

*Root description.*—Abundant, fleshy and white with finer lateral branches.

*Number of divisions or clumps per year.*—About eight 4-leaf cuttings per year.

*Durability of foliage to stresses.*—Foliage holds up well against damage from shipping and handling; plants are durable and have excellent indoor keeping quality.

*High temperature tolerance.*—About 104° F. (for several hours without damage.

*Low temperature tolerance.*—About 55° F. for several hours without damage.

Stems:

*Number of branches per plant.*—About 27.

*Type of branching.*—Basal.

*Length (from soil line to junction of the newest two leaves).*—12 cm.

*Diameter (measured 3 cm above the soil line).*—1.2 cm.

*Internode length (measured 3 cm above the soil line).*—1.0 cm to 2.2 cm.

*Color.*—Immature: Between RHS 159C to RHS 159D and tinged with RHS 49D. Mature: Between RHS 165C to RHS 165D. Oldest stems: RHS 161D and tinged with RHS 165D.

*Shape and appearance.*—Columnar, cylindrical and upright.

*Aspect.*—Vertical and upright.

*Strength.*—Sturdy and somewhat flexible.

*Axillary buds.*—Shape: Elliptic, flat to convex. Length: 0.5 cm. Width: 0.4 cm. Color: RHS 165C.

Leaves:

*Arrangement.*—Alternate and simple; the leaves are arranged in a spiral along the stem; the leaf blade folds upward along the midrib.

*Quantity of leaves per stem.*—8.

*Immature leaf (newly expanded leaf).*—Color: Upper surface: Base color is between RHS 146A to RHS 147A; the leaf blade is variably suffused with small RHS 145D and RHS 150D coalescing spots and blotches; areas adjacent to the midrib are RHS 145D and RHS 150D. Lower surface: Base color is between RHS N189A to RHS 147A and is tinged with colors between RHS 181B to RHS 181C; the upper surface patterns and markings are visible through to the lower surface of the leaf; the leaf blade is variably suffused with small coalescing spots and blotches between RHS 181B to RHS 181C; areas adjacent to the midrib are RHS 181C and tinged with RHS 50C.

*Mature leaf.*—Color: Upper surface: Base color is RHS 147A and the leaf blade is variably suffused with small coalescing spots and blotches between RHS 145D and RHS 150D (yellow-green); areas adjacent to the midrib are RHS 145D to RHS 150D. Lower surface: Base color is between RHS N189A to RHS 147A and is tinged with colors between RHS 181B to RHS 181C; the upper surface patterns and markings are visible through to the lower surface of the leaf; the leaf blade is variably suffused with small coalescing blotches and spots between RHS 181B to RHS 181C; areas adjacent to the midrib are RHS 181C and tinged with colors between RHS 50C and RHS 48A.

*Length.*—15 cm to 19 cm.

*Width.*—Flattened: 12 cm to 15 cm. Not flattened: 11.5 cm to 13.4 cm.

*Shape.*—Broadly ovate to round.

*Apex.*—Acuminate to cuspidate.

*Base.*—Cordate to somewhat obtuse.

*Margin.*—Smooth and entire with some broad undulations.

*Appearance.*—Smooth; new leaves are shiny and mature leaves are glossy; the leaf blade is convex between the main veins and puckered along the midrib resulting in a textured appearance.

*Pubescence (on both surfaces).*—Absent.

*Venation pattern.*—Pinnate.

*Venation color.*—Immature leaf (newly expanded leaf): Upper surface: Primary veins: RHS 55D. Midrib: RHS 54D. Lower surface: Primary veins: Between RHS 49A to RHS 49B and RHS 180D Midrib: Between RHS 48C to RHS 48D Mature leaf: Upper surface: Primary veins: Between RHS 51C to RHS 51D Midrib: Between RHS 53C to RHS 53D. Lower surface: Primary veins: Between RHS 51C to RHS 51D Midrib: Between RHS 51C to RHS 51D.

Petioles:

*Aspect.*—Vertical and upright when newly expanded and becoming curved outward to about 30 degrees to 45 degrees with maturity.

*Length.*—8.0 cm.

*Diameter.*—Distal: 0.45 cm. Proximal (petiole and petiole sheath clasps the stem proximally): Flattened: 2.7 cm. Not flattened: 0.8 cm to 1.2 cm.

*Color.*—Distal (between the top of the wing and the base of the leaf): RHS 54C tinged with RHS 54B. Proximal: RHS 54D and streaked with RHS 54B. Areas adjacent to the stem: RHS 49D.

*Wing.*—Length: 7.2 cm. Diameter: Mid-point: 0.8 cm. Base: 1.2 cm. Depth: 1.0 cm. Color: Inside: RHS 49D. Outside: RHS 54D and streaked with RHS 54B. Area adjacent to the stem: RHS 49D.

*Cataphylls.*—Length: 6.5 cm to 8.5 cm. Width: 1.5 cm. Shape: Lanceolate, two-keeled and translucent. Appearance: Inner surface is smooth and shiny and outer surface is glossy. Pubescence: Absent. Apex: Cuspidate. Base: Clasps the stem. Color: Inside and outside: the proximal end is between RHS 56C to RHS 56D and the distal end is RHS 50C.

Inflorescence:

*Appearance.*—Hooded spathes surrounding a columnar spadix are borne atop an upright peduncle; monoecious; the spadix is a central column of sessile, simple male and female flowers separated into two zones; the male flowers occupy the upper three-fourths of the spadix while the female flowers occupy the lower one-fourth of the spadix.

*Quantity of inflorescences per stem.*—About 3; each stem may have more than one inflorescence.

*Quantity of inflorescences per plant.*—About 10.

*Aspect.*—Upright.

*Height (from base of peduncle to tip of spathe).*—16 cm.

*Diameter/width.*—4.5 cm.

*Flowering habit.*—Seasonal; the natural flowering season is fall and winter as observed in Apopka, Fla.; the flowers are persistent.

*Fragrance.*—Absent.

*Ratio of inflorescence to opening.*—About 1 new flower every 10 to 14 days.

*Peduncle.*—Length: 9.5 cm. Diameter: 0.45 cm. Aspect: Upright. Strength: Sturdy and flexible. Color: RHS 161D.

Spathe:

*Appearance.*—Simple, hooded, cupped and enclosing the spadix; inflorescences have two partially developed spathes or one normal spathe enclosing the spadix; surface is smooth and shiny.

*Aspect.*—Upright.

*Shape.*—Elliptic.

*Apex.*—Acute.

*Margin.*—Entire.

*Pubescence* (*on the surfaces*).—Absent.

*Size.*—Length: 6.0 cm. Width: 2.2 cm (rolled).

*Color* (*when opening*).—Front side: RHS 161D and faintly mottled with RHS 146D. Rear side: RHS N170D and faintly mottled with RHS 146D.

*Color* (*fully opened*).—Front side: RHS 165D. Rear side: RHS 159A and tinged with RHS 144C and the apex is tinged with RHS 49C.

*Color* (*fading to*).—RHS 199B.

Spadix:

*Appearance and shape.*—Columnar.

*Aspect.*—Upright.

*Size.*—Length: 3.9 cm. Diameter of the female zone: 0.9 cm. Diameter of the male zone: 0.85 cm. Length of the female zone: 0.8 cm. Length of the male zone: 2.5 cm.

*Apex.*—Obtuse.

*Base.*—Obtuse.

*Margin.*—Pebbled.

*Color.*—Female zone (immature): RHS 4D. Male zone (immature): RHS 155D and RHS 150D. Female zone (mature): RHS 158B and RHS 160C. Male zone (mature): RHS 158C.

Flowers:

*Type.*—Simple.

*Quantity of female flowers per spadix.*—18.

*Quantity of male flowers per spadix.*—250.

*Shape of female.*—Ovate.

*Shape of male.*—Obovate, inverted triangle.

*Size.*—Female width: 0.2 cm. Male width: 0.15 cm. Female height and depth: 0.2 cm. Male height and depth: 0.2 cm.

Reproductive organs:

*Anther color.*—Not observed.

*Pollen amount.*—Not observed.

*Stigma color.*—Between RHS 158B to RHS 160C.

*Ovary color.*—RHS 145D;

Fruit and seed set: None observed.

Disease and insect resistance: Typical of *Aglaonema* species; no particular susceptibility or resistance to pests or diseases noted.

COMPARISON WITH KNOWN VARIETIES

'TWYAG0018' differs from the commercial variety 'Key Largo' (U.S. Plant Pat. No. 17,550) in that 'TWYAG60018' has broadly ovate to round leaves, while 'Key Largo' has oblong leaves. Additionally, 'TWYAG0018' has yellow-green spots and blotches on the foliage, while 'Key Largo' has silver colored flecks and spots on the foliage.

I claim:

1. A new and distinct cultivar of *Aglaonema* plant as shown and described herein.

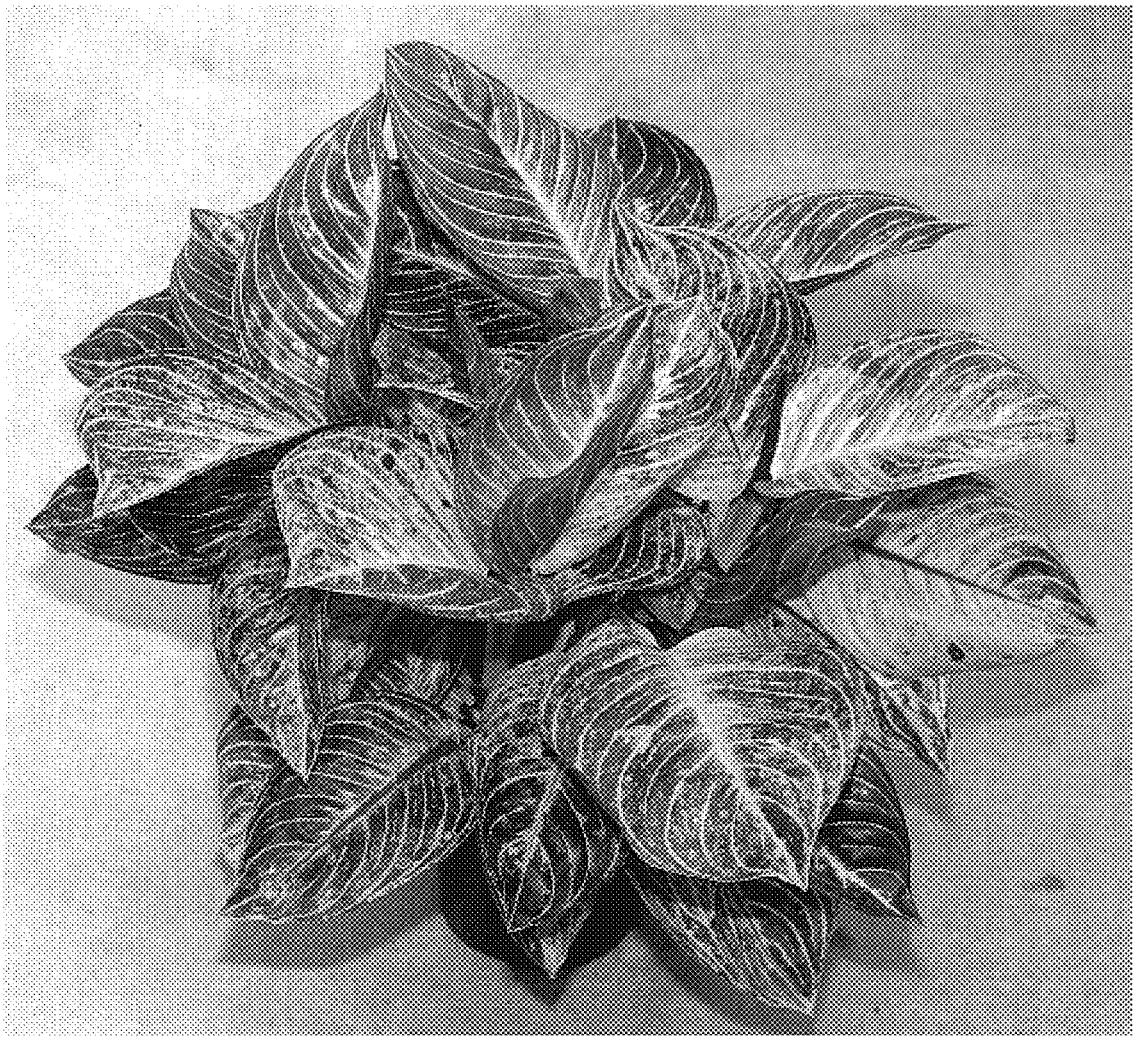

* * * * *